United States Patent
Suwalski et al.

(10) Patent No.: US 11,577,015 B2
(45) Date of Patent: Feb. 14, 2023

(54) CANNULA FOR MINIMALLY INVASIVE SURGICAL TRICUSPID VALVE REPAIR

(71) Applicant: MEDINICE S.A., Kielce (PL)

(72) Inventors: Piotr Suwalski, Warsaw (PL); Cezary Górniak, Piastów (PL)

(73) Assignee: MEDINICE S.A., Kielce (PL)

( * ) Notice: Subject to any disclaimer, the term of this patent is extended or adjusted under 35 U.S.C. 154(b) by 0 days.

(21) Appl. No.: 16/192,786

(22) Filed: Nov. 15, 2018

(65) Prior Publication Data
US 2020/0000996 A1   Jan. 2, 2020

(51) Int. Cl.
*A61M 1/36*   (2006.01)

(52) U.S. Cl.
CPC .................. *A61M 1/3659* (2014.02)

(58) Field of Classification Search
CPC ........ A61M 1/3659; A61M 2025/0004; A61M 25/007; A61M 25/0074; A61M 25/04; A61M 25/02; A61M 2025/0233; A61B 17/3417; A61B 17/3421; A61B 17/3423; A61B 2017/3419; A61B 2017/3433
See application file for complete search history.

(56) References Cited

U.S. PATENT DOCUMENTS

| | | | |
|---|---|---|---|
| 3,713,447 A * | 1/1973 | Adair | A61M 25/04 604/105 |
| 5,800,375 A | 9/1998 | Sweezer et al. | |
| 6,086,557 A | 7/2000 | Morejohn et al. | |
| 2001/0056273 A1 | 12/2001 | Ewers | |
| 2002/0107479 A1 | 8/2002 | Bates | |
| 2003/0167069 A1 * | 9/2003 | Gonzales | A61M 25/10 606/200 |
| 2004/0059293 A1 * | 3/2004 | Chu | A61M 25/04 604/107 |
| 2004/0087968 A1 * | 5/2004 | Core | A61B 17/3439 606/108 |
| 2011/0196190 A1 * | 8/2011 | Farnan | A61M 1/1008 600/16 |
| 2017/0189652 A1 * | 7/2017 | Loh | A61F 2/4611 |
| 2019/0255245 A1 * | 8/2019 | Kelly | A61M 1/3659 |

FOREIGN PATENT DOCUMENTS

| | | |
|---|---|---|
| CN | 102475556 A | 5/2012 |
| EP | 2138113 B1 | 3/2017 |

* cited by examiner

*Primary Examiner* — Kelly J Bekker
*Assistant Examiner* — Andrew P. Restaino
(74) *Attorney, Agent, or Firm* — Andrzej Malarz, Esq.

(57) ABSTRACT

A cannula for minimally invasive surgical tricuspid valve repair, which is constituted by a tube (5). equipped, at its distal end. with a head (2) consisting of a cone-shaped rigid ring (3) and connected to it on the other side of a flexible ring (4). where the flexible ring (4) in the folded state has a disk shape, and on top of the head (2) there is an axial hole (8) leading to the interior of the cannula (1). and where on the whole length of the head (2) and on a part of the tube (5) near the connection to the head (2), from the inside, there is a thin guide sleeve (6) which, on the section of the rigid ring (3) is permanently attached to the surface of its wall, while on its remaining length, it is slidably movable relative to the wall of the tube (5).

6 Claims, 2 Drawing Sheets

CANNULA FOR MINIMALLY INVASIVE SURGICAL TRICUSPID VALVE REPAIR

TECHNICAL FIELD

The object of the invention is a cannula for minimally invasive surgical tricuspid valve repair.

BACKGROUND ART

Cannulation is a procedure for placing a cannula, i.e. a special tube in the arterial vessel, most often in the aorta or the femoral artery, and in the venous vessel for receiving and feeding blood from a patient to the apparatus providing extracorporeal circulation. For the surgeries on tricuspid valve, it is necessary to selectively cannulate both the superior vena cava (SVC) and the inferior vena cava (IVC) so that blood does not flow through the right atrium, which allows opening thereof and reaching the tricuspid valve undergoing surgery. In the standard procedure of tricuspid valve repair, blood flow to and from the SVC and the IVC is cut off before the blood reaches the right atrium. This procedure is necessary to isolate the right atrium with the tricuspid valve, and at the same time to protect other organs and tissues from death. Method of isolation, i.e. closing, clamping of the main veins around the cannula so that the blood flows only inside the cannula and not through the lumen of the vessel is essential for the cannulation. Clamping from outside by means of so-called snuggers is typical for standard surgeries i.e. by sternotomy. However, it can be very difficult or even impossible in the case of minimally invasive surgeries consisting of accessing the heart and valve by an incision having a few centimetres in the side wall of the chest without affecting the bones and of replacing the valve under the control of an endoscopic camera using special long tools. Such surgeries are associated with a different method of connecting the extracorporeal circulation, with another place of cannulation (vein and femoral artery in the groin) and, therefore, with the need to use completely different cannulas.

On the market, there are venous cannulas for minimally invasive surgery. Adding a balloon or a special collar to the cannula in its distal part, which allows the main vein to be closed somewhat from the inside, gives the same effect as clamping the vein from the outside and, therefore, allows minimally invasive surgery.

Normally, two cannulas are used for minimally invasive tricuspid valve surgery, one for the inferior vena cava, which is inserted into the femoral artery, and the other for the superior vena cava, which is inserted through the jugular vein. However, attempts have been made to develop a cannula design which would drain blood from both veins at the same time.

So, from No. U.S. Pat. No. 6,086,557, a venous cannula is known which is intended to drain the patient's blood during cardiac surgery and has two branches at the end of the main part of the cannula. Around the middle of each branch, there is an occlusive balloon which, after filling, seals the blood vessel from the inside and, thereby, prevents blood flow along the cannula on its outer side.

From U.S. Pat. No. 5,800,375, a cannula and a method of cannulation of blood vessels during heart surgery are known. The cannula is equipped with two occlusive balloons sealing the main vein from the inside.

From patent application No. CN102475556, a cannula for the main vein is known which has an umbrella-shaped ring made of a soft silicone.

SUMMARY

The essence of the invention consists in that the cannula is formed by a tube equipped at its proximal end with a head consisting of a cone-shaped rigid ring connected on the other side by a flexible ring which in the folded state has a disk shape, wherein on top of the head there is an axial hole leading to the interior of the cannula. On the whole length of the head and on a tube part near the connection to the head, from the inside, there is a thin guide sleeve which, on the section of the rigid ring, is permanently attached to the surface of its wall, while on its remaining length, it is slidably movable relative to the wall of the cannula. The guide sleeve is equipped with at least two tie rods attached, on one end, opposite to each other, to the wall of the guide sleeve, and their free ends extend along walls of the cannula beyond its distal end.

Preferably, the diameter of an inlet hole at the top of the head constitutes from 50 to 90% of the outer diameter of the cannula.

Preferably, on the central section of the cannula with a length of 10 to 20%, there are transverse holes in the walls evenly spaced around its circumference.

Advantages

The greatest advantage of the solution according to the invention is the fact that it allows, under conditions of minimally invasive cardiac surgery, selective draining of blood from the inferior and superior vena cava, which is necessary for tricuspid valve surgery. The cannula according to the invention is introduced only through the femoral vein, without the need for cannulation of other vessels (for example the jugular vein), and also does not require sealing from the outside of the cannula in the superior vena cava, which is a time-consuming procedure, and in certain anatomical and clinical conditions, for example in the case of reoperation surgery, is risky and impossible to conduct.

The cannula application is relatively simple and undoubtedly reduces the surgery time, which is of great importance for the condition of the cardiac patient and for the speed of his recovery after procedure. Head design allows for efficient passage through the veins, and at the same time it allows for tight cutting off of the blood flow to the right atrium. Variable outer diameter of the head gives the possibility to adjust its size to the inner diameter of the vein. The superiority of the cannula according to the invention over cannulas in which the seal is in the form of a balloon is such that there is not any need to fill the balloon, which is a time-consuming and difficult activity, and the sealing effect is the same.

The simple design of the cannula according to the invention will also be important for the cost of its manufacture, and therefore for the final price.

BRIEF DESCRIPTION OF THE DRAWINGS

The object of the invention is presented in exemplary embodiment in the following drawings, wherein.

DETAILED DESCRIPTION

Figures 1, 2, 3, 4:
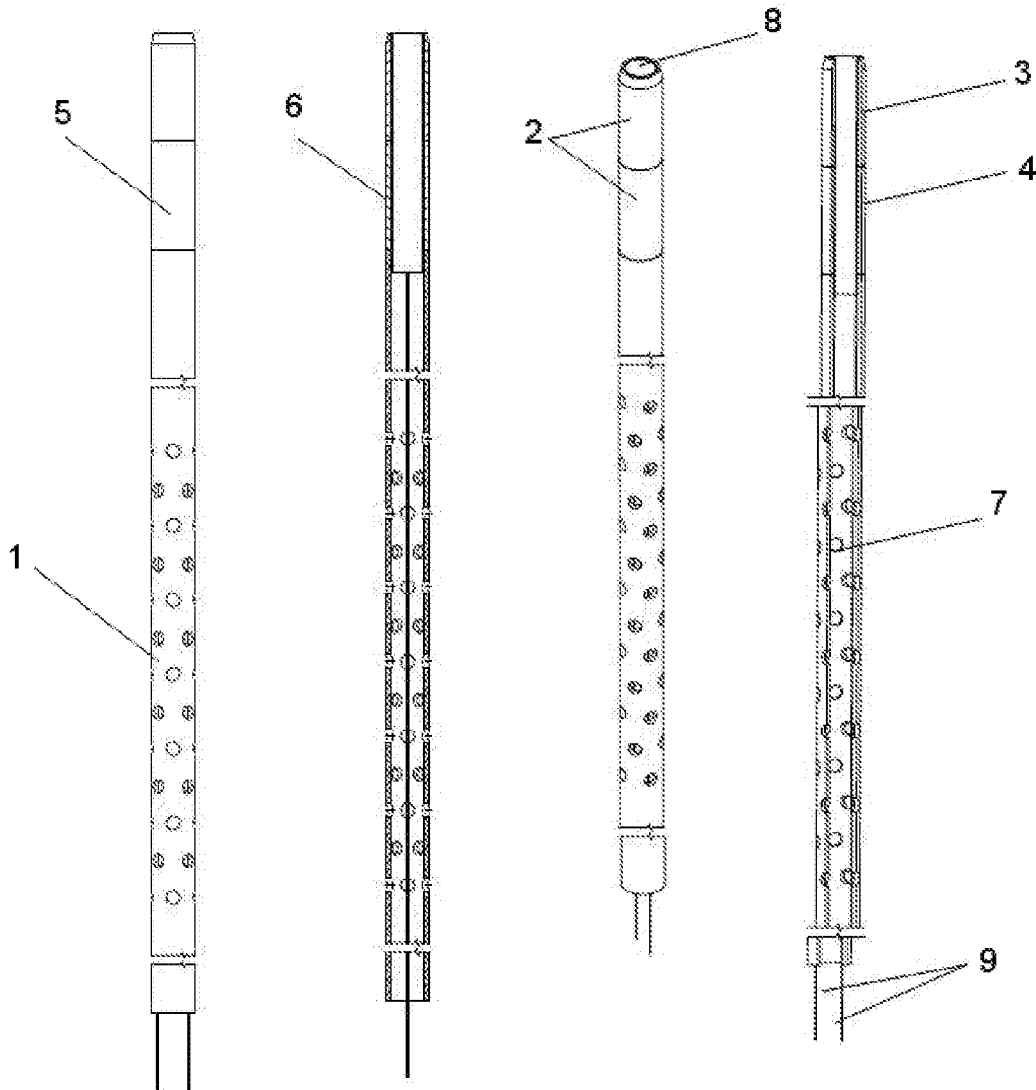
FIG. 1 is a side view of the cannula, FIG. 2—a longitudinal section of the cannula, FIG. 3—an axonometric view of the cannula, FIG. 4—a half-view-half-section of the cannula, FIG. 5—a side view of the cannula,
FIG. 6—a cross-section of the cannula,
FIG. 7—an axonometric view of the cannula, and
FIG. 8—a half-view-half-section of the cannula.
Figures 5, 6, 7, 8:
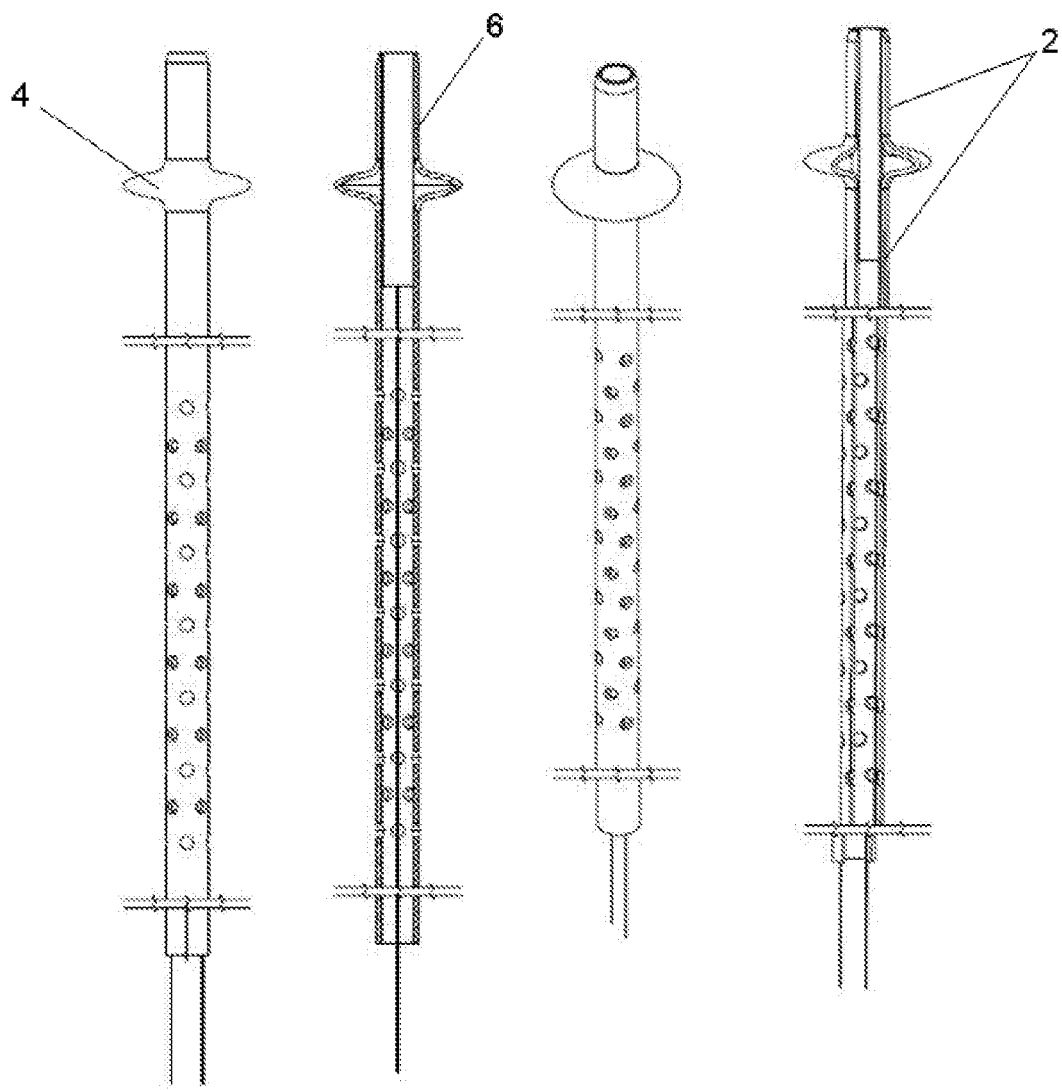

The cannula 1 is constituted by a tube 5 equipped, at a proximal end, with a head 2 consisting of a cone-shaped rigid ring 3 and connected to it, on the other side, by means of a flexible ring 4 which in the folded state has a disk shape. At the top of the head 2, there is an axial hole 8 leading to the interior of the cannula 1, the diameter of which constitutes 80% of the outer diameter of the cannula. On the whole length of the head 2 and on a part of the tube 5 near the connection to the head 2, from the inside, there is a thin guide sleeve 6 which, on the section of the rigid ring 3, is permanently attached to the surface of its wall, while on its remaining length, it is slidably movable relative to the wall of the tube 5. The guide sleeve 6 is equipped with two tie rods 9 attached, on one end, opposite to each other, to the wall of the guide sleeve 6, and their free ends extend along walls of the cannula 1 beyond its distal end and are terminated with ergonomic handles. On the central section of the cannula 1 with a length of 10 to 20%, there are transverse holes 7 in the walls evenly spaced around its circumference.

The cannula 1 with its head 2 unfolded is introduced into the femoral vein, then, having reached the heart, the right vestibule is passed, and the head 2 of the cannula 1 is placed in the superior vena cava. Then, pulling on the tie rods 9 causes the rigid ring 3 to be pressed against the flexible ring 4 and its wall to bulge outwardly. A connector, located at the distal end of the cannula 1, is connected to the apparatus providing extracorporeal circulation. After surgery, the wall of the flexible ring 4 is straightened out by means of the tie rods 9, after which the cannula 1 is removed from the vein.

LIST OF REFERENCE NUMERALS

1—cannula
2—head
3—rigid ring
4—flexible ring
5—tube
6—guide sleeve
7—transverse hole
8—inlet hole to the interior of the cannula
9—tie rod

The invention claimed is:
1. A cannula, comprising
a flexible tube (5) having a proximal end that comprises a connector, wherein
the tube (5) comprises a head (2) at a distal end of the tube (5), wherein the head (2) comprises a truncated cone-shaped rigid ring (3) and a flexible ring (4) which in a folded state has a disk shape and is connected to a proximal end of the rigid ring (3), wherein on the distal end of the head (2) there is an axial hole (8), leading to a interior of the cannula (1), wherein
a thin guide sleeve (6) is positioned inside the entire length of the rigid ring (3) and the flexible ring (4) of the head (2) and on a part of the tube (5) near the connection to the flexible ring (4) of the head (2), wherein
a variable outer diameter of the head (2) allows adjustment of its size to an inner diameter of a vein, wherein
the thin guide sleeve (6) is permanently attached to an inner surface of a wall of the rigid ring (3) on a section of the rigid ring (3), wherein the thin guide sleeve (6) is slidably movable relative to an inner surface of a wall of the tube (5) on a remaining section of the tube, wherein
the guide sleeve (6) is equipped with at least two tie rods (9) attached, on the one end, opposite to each other, to a wall of the guide sleeve (6), wherein free ends of the tie rods (9) extend along walls of the cannula (1) beyond the proximal end of the cannula (1), terminated with ergonomic handles, and wherein the flexible ring (4) has a uniform and an uninterrupted structure.
2. The cannula according to claim 1, wherein a diameter of the axial hole (8) at the top of the head (2) of the tube at a longitudinal end, comprises from 50 to 90% of an outer diameter of the cannula (1).
3. The cannula according to claim 1, wherein on a central section of the cannula (1) with a length of 10 to 20 centimeters, there are transverse holes (7) in walls evenly spaced around a circumference of the central section of the cannula.
4. The cannula according to claim 1, wherein the cannula is introduced only through a femoral vein without a need for cannulation of other vessels.
5. The cannula according to claim 1, wherein the cannula does not require sealing from outside of the cannula in the superior vena cava.
6. The cannula according to claim 1, wherein a design of the head (2) allows for efficient passage through the veins, and at the same time allows for tight cutting off of the blood flow to a right atrium.

* * * * *